United States Patent
Nobe et al.

(10) Patent No.: US 8,093,419 B2
(45) Date of Patent: Jan. 10, 2012

(54) METHOD OF PRODUCING ORGANOSILICON COMPOUND

(75) Inventors: Youhei Nobe, Ibaraki (JP); Hisashi Nakagawa, Belmont, MA (US); Kang-go Chung, Ibaraki (JP)

(73) Assignee: JSR Corporation, Tokyo (JP)

( * ) Notice: Subject to any disclaimer, the term of this patent is extended or adjusted under 35 U.S.C. 154(b) by 392 days.

(21) Appl. No.: 12/473,861

(22) Filed: May 28, 2009

(65) Prior Publication Data

US 2009/0299086 A1  Dec. 3, 2009

(30) Foreign Application Priority Data

May 30, 2008 (JP) ................................. 2008-142379
Mar. 30, 2009 (JP) ................................. 2009-081033

(51) Int. Cl.
*C07F 7/08* (2006.01)
(52) U.S. Cl. ...................................................... 556/443
(58) Field of Classification Search .................. 556/443
See application file for complete search history.

(56) References Cited

U.S. PATENT DOCUMENTS

| | | | |
|---|---|---|---|
| 7,291,567 B2 | 11/2007 | Tsuchiya et al. |
| 7,399,715 B2 | 7/2008 | Tsuchiya et al. |
| 7,462,678 B2 | 12/2008 | Akiyama et al. |
| 7,514,151 B2 | 4/2009 | Shiota |
| 7,528,207 B2 | 5/2009 | Nakagawa et al. |
| 2006/0210812 A1 | 9/2006 | Shiota |
| 2007/0015892 A1 | 1/2007 | Nakagawa et al. |
| 2007/0020467 A1 | 1/2007 | Nakagawa et al. |
| 2007/0027287 A1 | 2/2007 | Akiyama et al. |
| 2007/0031687 A1 | 2/2007 | Akiyama et al. |
| 2008/0038527 A1 | 2/2008 | Akiyama et al. |
| 2008/0268264 A1 | 10/2008 | Akiyama et al. |

FOREIGN PATENT DOCUMENTS

WO  WO 2005/068539 A1  7/2005

OTHER PUBLICATIONS

Wanzhi Chen et al, Chemistry Letters, 2001, 1096-1097.*
U.S. Appl. No. 12/934,806, filed Sep. 27, 2010, Nakagawa, et al.
U.S. Appl. No. 12/717,225, filed Mar. 4, 2010, Akiyama, et al.
U.S. Appl. No. 12/749,735, filed Mar. 30, 2010, Nobe, et al.
U.S. Appl. No. 12/093,254, filed May 9, 2008, Hisashi Nakagawa, et al.
U.S. Appl. No. 12/278,224, filed Aug. 4, 2008, Hisashi Nakagawa, et al.

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

A method of producing an organosilicon compound includes substituting at least an $OR^1$ group of a compound shown by the following general formula (1) to obtain a compound shown by the following general formula (2), $$Si(OR^1)_{3-m}Y^1{}_m\text{—}R^2\text{—}Si(OR^3)_{3-n}Y^2{}_n \quad (1)$$

$$Si(OR^4)_{3-m}Y^1{}_m\text{—}R^2\text{—}Si(OR^4)_{3-n}Y^2{}_n \quad (2).$$

8 Claims, No Drawings

METHOD OF PRODUCING ORGANOSILICON COMPOUND

Japanese Patent Application No. 2008-142379 filed on May 30, 2008 and Japanese Patent Application No. 2009-81033 filed on Mar. 30, 2009, are hereby incorporated by reference in their entirety.

BACKGROUND OF THE INVENTION

The present invention relates to a method of producing an organosilicon compound.

A silicon compound having a hydrolyzable group such as an alkoxy group or a halogen atom is used as an inorganic polymer material precursor or a CVD raw material. A film formed using an organosilicon compound having a skeleton in which two silicon atoms are bonded via at least one carbon atom has excellent chemical and mechanical properties (e.g., heat resistance, chemical resistance, conductivity, and modulus of elasticity) (see WO2005/068539).

An organosilicon compound having a skeleton in which two silicon atoms are bonded via a carbon atom may be synthesized by hydrosilylation using a transition metal as a catalyst, or forming a silicon-carbon bond by a nucleophilic reaction (Grignard reaction) using an alkali metal, for example. WO2005/068539 discloses a method of producing an organosilicon compound that includes reacting methyltrimethoxysilane with a Grignard reagent obtained by reacting (chloromethyl)trimethylsilane with magnesium to obtain [trimethylsilyl][methyl]methyldimethoxysilane.

However, when producing an organosilicon compound in which each of two silicon atoms has a hydrolyzable group using the method disclosed in WO2005/068539, it is necessary to control the conditions for suppressing polymerization due to a side reaction since the hydrolyzable group has high reactivity. When synthesizing an Si—C—Si skeleton-containing silicon compound having an alkoxy group on each end, it is not necessarily easy to arbitrarily control the number of alkoxy groups on each end. Therefore, development of a versatile method that can easily synthesize an Si—C—Si skeleton-containing silicon compound having a hydrolyzable group (e.g., alkoxy group) on each end has been desired.

An object of the invention is to provide a method of producing an organosilicon compound by which a product can be obtained in high yield by a simple step while reducing the reaction time as compared with a synthesis process using only a Grignard reaction.

SUMMARY

According to one aspect of the invention, there is provided a method of producing an organosilicon compound comprising substituting at least an $OR^1$ group of a compound shown by the following general formula (1) to obtain a compound shown by the following general formula (2), $$Si(OR^1)_{3-m}Y^1{}_m\text{—}R^2\text{—}Si(OR^3)_{3-n}Y^2{}_n \quad (1)$$

wherein $R^1$ individually represents a substituted or unsubstituted alkyl group having 3 to 10 carbon atoms, a substituted or unsubstituted alkenyl group having 3 to 10 carbon atoms, a substituted or unsubstituted alkynyl group having 3 to 10 carbon atoms, or a substituted or unsubstituted aryl group having 6 to 12 carbon atoms, $Y^1$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, $R^2$ individually represents a substituted or unsubstituted methylene group, a substituted or unsubstituted alkylene group having 2 to 6 carbon atoms, a substituted or unsubstituted alkenylene group having 2 to 6 carbon atoms, a substituted or unsubstituted alkynylene group having 2 to 6 carbon atoms, or a substituted or unsubstituted arylene group having 6 to 12 carbon atoms, m represents an integer from 0 to 2, $R^3$ individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group having 6 to 12 carbon atoms, or a substituted or unsubstituted acyl group having 1 to 10 carbon atoms, $Y^2$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, and n represents an integer from 0 to 2, $$Si(OR^4)_{3-m}Y^1{}_m\text{—}R^2\text{—}Si(OR^4)_{3-n}Y^2{}_n \quad (2)$$

wherein $R^4$ individually represents an alkyl group having 1 or 2 carbon atoms or an alkenyl group, and $R^2, Y^1, Y^2$, m, and n are the same as defined for the general formula (1).

The above method of producing an organosilicon compound may further comprise reacting at least one compound shown by the following general formula (3) with a compound shown by the following general formula (4) to obtain the compound shown by the general formula (1), $$Si(OR^1)_{3-m}Y^1{}_m\text{—}R^2\text{-}M^1X \quad (3)$$

wherein $R^1, R^2, Y^1$, and m are the same as defined for the general formula (1), $M^1$ represents an alkali metal or an alkaline earth metal, and X represents a halogen atom, $$Si(OR^3)_{4-n}Y^2{}_n \quad (4)$$

wherein $R^3, Y^2$, and n are the same as defined for the general formula (1).

In this case, the method may further comprise causing a compound shown by the following general formula (5) to undergo a reaction in the presence of at least one of an alkali metal and an alkaline earth metal to obtain the compound shown by the general formula (3), $$Si(OR^1)_{3-m}Y^1{}_m\text{—}R^2\text{—}R^2\text{—}X \quad (5)$$

wherein $R^1, R^2, Y^1$, and m are the same as defined for the general formula (1), and X is the same as defined for the general formula (3).

In this case, the alkaline earth metal may be magnesium.

In the above method of producing an organosilicon compound, the $OR^1$ group may be substituted by reacting the compound shown by the general formula (1) with at least one of a compound shown by the following general formula (6) and a compound shown by the following general formula (7), $$R^4OH \quad (6)$$

wherein $R^4$ is the same as defined for the general formula (2), $$(R^4O)_rM^2 \quad (7)$$

wherein $M^2$ represents an alkali metal or an alkaline earth metal, r represents the valence of the alkali metal or the alkaline earth metal represented by $M^2$, and $R^4$ is the same as defined for the general formula (2).

In the above method of producing an organosilicon compound, the $OR^1$ group may be substituted in the presence of an acid catalyst or an alkali catalyst.

In the above method of producing an organosilicon compound, $R^2$ in the general formula (1) and the general formula (2) may be a methylene group.

In the above method of producing an organosilicon compound, $R^4$ in the general formula (2) may be a methyl group.

According to another aspect of the invention, there is provided a method of producing an organosilicon compound comprising reacting at least one compound shown by the general formula (3) with the compound shown by the general formula (4) to obtain the compound shown by the general formula (1).

According to the above method of producing an organosilicon compound, a product (i.e., the compound shown by the general formula (2)) can be obtained in high yield by a simple step while reducing the reaction time as compared with a synthesis process using only a Grignard reaction.

DETAILED DESCRIPTION OF THE EMBODIMENT

An organosilicon compound and a method of producing the same according to one embodiment of the invention are described in detail below.

1. Organosilicon Compound and Method of Producing the Same

1.1. Method of Producing Organosilicon Compound

A method of producing an organosilicon compound according to one embodiment of the invention includes substituting at least an $OR^1$ group of a compound shown by the following general formula (1) (hereinafter may be referred to as "compound 1") to obtain a compound shown by the following general formula (2) (hereinafter may be referred to as "compound 2").

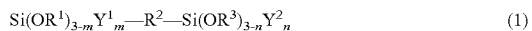  (1)

wherein $R^1$ individually represents a substituted or unsubstituted alkyl group having 3 to 10 carbon atoms, a substituted or unsubstituted alkenyl group having 3 to 10 carbon atoms, a substituted or unsubstituted alkynyl group having 3 to 10 carbon atoms, or a substituted or unsubstituted aryl group having 6 to 12 carbon atoms, $Y^1$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, $R^2$ individually represents a substituted or unsubstituted methylene group, a substituted or unsubstituted alkylene group having 2 to 6 carbon atoms, a substituted or unsubstituted alkenylene group having 2 to 6 carbon atoms, a substituted or unsubstituted alkynylene group having 2 to 6 carbon atoms, or a substituted or unsubstituted arylene group having 6 to 12 carbon atoms, m represents an integer from 0 to 2, $R^3$ individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group having 6 to 12 carbon atoms, or a substituted or unsubstituted acyl group having 1 to 10 carbon atoms, $Y^2$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, and n represents an integer from 0 to 2.

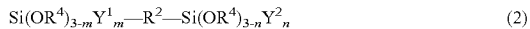  (2)

wherein $R^4$ individually represents an alkyl group having 1 or 2 carbon atoms or an alkenyl group, and $R^2$, $Y^1$, $Y^2$, m, and n are the same as defined for the general formula (1).

Examples of the substituted or unsubstituted alkyl group having 3 to 10 carbon atoms represented by $R^1$ in the general formulas (1) and (2) include an n-propyl group, an isopropyl group, an n-butyl group, an isobutyl group, a tert-butyl group, a pentyl group, an isopentyl group, a hexyl group, a heptyl group, an octyl group, a nonyl group, a decyl group, and the like. Examples of the substituted or unsubstituted alkenyl group having 3 to 10 carbon atoms represented by $R^1$ include an allyl group, a butenyl group, a hexenyl group, and the like. Examples of the substituted or unsubstituted alkynyl group having 3 to 10 carbon atoms represented by $R^1$ include a propynyl group and the like. Examples of the substituted or unsubstituted aryl group having 6 to 12 carbon atoms represented by $R^1$ include a phenyl group, a tolyl group, a naphthyl group, and the like. The alkyl group, the alkenyl group, the alkynyl group, and the aryl group may be substituted by a halogen atom or the like.

Examples of the substituted or unsubstituted alkylene group having 2 to 6 carbon atoms represented by $R^2$ in the general formulas (1) and (2) include a dimethylene group, a trimethylene group, a tetramethylene group, a pentamethylene group, a hexamethylene group, and the like. Examples of the substituted or unsubstituted alkenylene group having 2 to 6 carbon atoms represented by $R^2$ include a vinylene group, a 1-methylvinylene group, a propenylene group, a 1-butenylene group, a 2-butenylene group, a 1-pentenylene group, a 2-pentenylene group, and the like. Examples of the substituted or unsubstituted alkynylene group having 2 to 6 carbon atoms represented by $R^2$ include an ethynylene group, a propynylene group, a 2-butynylene group, and the like. Examples of the substituted or unsubstituted arylene group having 6 to 12 carbon atoms represented by $R^2$ include a phenylene group, a naphthylene group, and the like. A hydrogen atom included in the alkyl group, the alkenyl group, the alkynyl group, the aryl group, the acyl group, the methylene group, the alkylene group, the alkenylene group, the alkynylene group, and the arylene group may be substituted by a halogen atom or the like.

Examples of the substituted or unsubstituted alkyl group having 1 to 10 carbon atoms represented by $R^3$ in the general formulas (1) and (2) include a methyl group, an ethyl group, an n-propyl group, an isopropyl group, an n-butyl group, an isobutyl group, a tert-butyl group, a pentyl group, an isopentyl group, a hexyl group, a heptyl group, an octyl group, a nonyl group, a decyl group, and the like. Examples of the substituted or unsubstituted alkenyl group having 2 to 10 carbon atoms represented by $R^3$ include a vinyl group, an allyl group, a butenyl group, a hexenyl group, and the like. Examples of the substituted or unsubstituted alkynyl group having 2 to 10 carbon atoms represented by $R^3$ include an ethynyl group, a propynyl group, and the like. Examples of the substituted or unsubstituted aryl group having 6 to 12 carbon atoms represented by $R^3$ include a phenyl group, a tolyl group, a naphthyl group, and the like. Examples of the substituted or unsubstituted acyl group having 1 to 10 carbon atoms represented by $R^3$ include a formyl group, an acetyl group, a propionyl group, a butyryl group, and the like.

Examples of the substituted or unsubstituted alkyl group having 1 to 10 carbon atoms represented by $Y^1$ and $Y^2$ in the general formulas (1) and (2) include a methyl group, an ethyl group, an n-propyl group, an isopropyl group, an n-butyl group, an isobutyl group, a tert-butyl group, a pentyl group, an isopentyl group, a hexyl group, a heptyl group, an octyl group, a nonyl group, a decyl group, and the like. Examples of the substituted or unsubstituted alkenyl group having 2 to 10 carbon atoms represented by $Y^1$ and $Y^2$ include a vinyl group, an allyl group, a butenyl group, a hexenyl group, and the like. Examples of the substituted or unsubstituted alkynyl group having 2 to 10 carbon atoms represented by $Y^1$ and $Y^2$ include an ethynyl group, a propynyl group, and the like. Examples of the substituted or unsubstituted aryl group having 6 to 12 carbon atoms represented by $Y^1$ and $Y^2$ include a phenyl group, a tolyl group, a naphthyl group, and the like.

It is preferable that one of m and n in the general formulas (1) and (2) be one or more. It is more preferable that m and n be one or two, and more preferably one.

$R^1$ in the general formula (1) is preferably an n-propyl group, an isopropyl group, an n-butyl group, an isobutyl group, a tert-butyl group, a pentyl group, an isopentyl group, a hexyl group, a heptyl group, an octyl group, a nonyl group, an allyl group, a butenyl group, or a hexenyl group, and more preferably an isopropyl group, an n-butyl group, an isobutyl group, a tert-butyl group, a pentyl group, or an isopentyl group.

$Y^1$ is preferably a methyl group, an ethyl group, an n-propyl group, a vinyl group, or a phenyl group. $R^2$ is preferably a methylene group. X is preferably a chlorine atom or a bromine atom.

$R^3$ in the general formula (1) is preferably a methyl group, an ethyl group, an n-propyl group, or an isopropyl group, and more preferably a methyl group, an ethyl group, or an isopropyl group.

$Y^2$ is preferably a methyl group, an ethyl group, an n-propyl group, or an isopropyl group.

$R^4$ in the general formula (2) is particularly preferably a methyl group.

1.2. Production of Compound 2

In the method of producing the organosilicon compound according to this embodiment, the group represented by $OR^1$ of the compound 1 can be substituted with the group represented by $OR^4$ when obtaining the compound 1 from the compound 2. In this procedure, the group represented by $OR^3$ of the compound 1 can be also substituted with the group represented by $OR^4$ at the same time.

In the method of producing the organosilicon compound according to this embodiment, the group represented by $OR^1$ is preferably at least one group selected from an alkoxy group having 3 to 10 carbon atoms, an alkenyloxy group, and a phenyloxy group.

In the method of producing the organosilicon compound according to this embodiment, the group represented by $OR^1$ is preferably substituted by reacting the compound 1 with at least one of a compound shown by the following general formula (6) (hereinafter may be referred to as "compound 6") and a compound shown by the following general formula (7) (hereinafter may be referred to as "compound 7") to obtain the compound 2. The group represented by $OR^1$ is preferably substituted in the presence of an acid catalyst or an alkali catalyst. When substituting the group represented by $OR^1$ using the compound 6, the group represented by $OR^1$ is preferably substituted in the presence of the acid catalyst. For example, the compound 1 is mixed with at least one of the compound 6 and the compound 7, and the acid catalyst or the alkali catalyst is optionally added to effect a reaction.

$$R^4OH \quad (6)$$

wherein $R^4$ is the same as defined for the general formula (2).

$$(R^4O)_rM^2 \quad (7)$$

wherein $M^2$ represents an alkali metal or an alkaline earth metal, r represents the valence of the alkali metal or the alkaline earth metal represented by $M^2$, and $R^4$ is the same as defined for the general formula (2).

The compound 6 may be methanol, ethanol, or both.

The compound 7 may be sodium methoxide, sodium ethoxide, potassium methoxide, or potassium ethoxide.

Examples of the acid catalyst include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, maleic anhydride, fumaric acid, itaconic acid, succinic acid, mesaconic acid, citraconic acid, malic acid, malonic acid, a hydrolysate of glutaric anhydride, a hydrolysate of maleic anhydride, a hydrolysate of phthalic anhydride, and the like. Examples of an inorganic acid used as the acid catalyst include hydrochloric acid, nitric acid, sulfuric acid, fluoric acid, phosphoric acid, and the like.

Examples of the alkali catalyst include methoxymethylamine, methoxyethylamine, methoxypropyl amine, methoxybutyl amine, ethoxymethylam ine, ethoxyethylamine, ethoxypropylamine, ethoxybutylamine, propoxymethylamine, propoxyethylamine, propoxypropylamine, propoxybutylamine, butoxymethylamine, butoxyethylamine, butoxypropylamine, butoxybutylamine, methylamine, ethylamine, propylamine, butylamine, N,N-dimethylamine, N,N-diethylamine, N,N-dipropylamine, N,N-dibutylamine, trimethylamine, triethylamine, tripropylamine, tributylamine, tetramethylethylenediamine, tetraethylethylenediamine, tetrapropylethylenediamine, tetrabuthylethylenediamine, methylaminomethylamine, methylaminoethylamine, methylaminopropylamine, methylaminobutylamine, ethylaminomethylamine, ethylaminoethylamine, ethylaminopropylamine, ethylaminobutylamine, propylaminomethylamine, propylaminoethylamine, propylaminopropylamine, propylaminobutylamine, butylaminomethylamine, butylaminoethylamine, butylaminopropylamine, butylaminobutylamine, tetramethylammonium bromide, tetramethylammonium chloride, tetraethylammonium bromide, tetraethylammonium chloride, tetra-n-propylammonium bromide, tetra-n-propylammonium chloride, tetra-n-butylammonium bromide, tetra-n-butylammonium chloride, n-octadecyltrimethylammonium bromide, cetyltrimethylammonium chloride, stearyltrimethylammonium chloride, benzyltrimethylammonium chloride, didecyldimethylammonium chloride, distearyldimethylammonium chloride, tridecylmethylammonium chloride, tetrabutylammonium hydrogen sulfate, tributylmethylammonium bromide, trioctylmethylammonium chloride, trilaurylmethylammonium chloride, benzyltriethylammonium bromide, benzyltributylammonium bromide, phenyltrimethylammonium bromide, choline, pyridine, pyrrole, piperazine, pyrrolidine, piperidine, picoline, morpholine, methylmorpholine, diazabicyclooctane, diazabicyclononane, diazabicycloundecene, ammonia, and the like.

When reacting the compound 1 with the compound 6, the compound 1 and the compound 6 are preferably mixed so that the amount of the compound 6 is 3 to 20 mol, and more preferably 5 to 10 mol, based on 1 mol of the compound 1. The reaction temperature is preferably 0 to 50° C., and more preferably 10 to 40° C.

1.3. Production of Compound 1

The method of producing the organosilicon compound according to this embodiment may further include reacting at least one compound shown by the following general formula (3) (hereinafter may be referred to as "compound 3") with a compound shown by the following general formula (4) (hereinafter may be referred to as "compound 4") to obtain the compound shown by the general formula (1). A method of producing an organosilicon compound according to another embodiment of the invention includes reacting the compound 3 with the compound 4 to obtain the compound 1. For example, the compound 5 may be added to a solution containing the compound 3 to effect a reaction.

$$Si(OR^1)_{3-m}Y^1{}_m—R^2—MgX \quad (3)$$

wherein $R^1$, $R^2$, $Y^1$, and m are the same as defined for the general formula (1), and X represents a halogen atom.

$$Si(OR^3)_{4-n}Y^2{}_n \quad (4)$$

wherein $R^3$, $Y^2$, and n are the same as defined for the general formula (1).

When reacting the compound 3 with the compound 4 to obtain the compound 1, the compound 3 has a function of a Grignard reagent so that the compound 1 having an Si—$R^2$—Si skeleton is obtained by the Grignard reaction between the compound 3 and the compound 4.

When the $OR^1$ group of the compound 3 has steric hindrance higher than that of the $OR^3$ group of the compound 4, self-condensation of the compound 3 can be suppressed more effectively when reacting the compound 3 with the compound 4. Therefore, since the Grignard reaction between the compound 3 and the compound 4 proceeds easily, the compound 1 can be obtained almost as a single product. Accordingly, it is preferable that the number of carbon atoms of the $OR^1$ group be larger than that of the $OR^3$ group.

When reacting the compound 3 with the compound 4, the compound 3 and the compound 4 are preferably mixed so that the amount of the compound 4 is 0.7 to 10 mol, and more preferably 0.8 to 3 mol, based on 1 mol of the compound 3. The reaction temperature is preferably 0 to 250° C., and more preferably 40 to 150° C.

It is preferable to use an ether solvent when producing the compound 1. Examples of the ether solvent include diethyl ether, di-n-propyl ether, diisopropyl ether, dibutyl ether, ethyl propyl ether, anisole, phenetole, diphenyl ether, diethylene glycol dimethyl ether, diethylene glycol diethyl ether, diethylene glycol dibutyl ether, diethylene glycol methyl ethyl ether, dipropylene glycol dimethyl ether, dipropylene glycol diethyl ether, dipropylene glycol dibutyl ether, dipropylene glycol methyl ethyl ether, ethylene glycol dimethyl ether, ethylene glycol diethyl ether, ethylene glycol dibutyl ether, ethylene glycol methyl ethyl ether, propylene glycol dimethyl ether, propylene glycol diethyl ether, propylene glycol dibutyl ether, propylene glycol methyl ethyl ether, tetrahydrofuran, dioxane, and the like. Among these, diethyl ether, tetrahydrofuran, ethylene glycol dimethyl ether, and ethylene glycol diethyl ether are preferable from the viewpoint of excellent solubility for the compound 3 and the compound 4.

1.3.1. Raw Material (Compound 3)

In the method of producing the organosilicon compound according to this embodiment, the compound 3 that is the raw material for the compound 1 may be obtained by causing a compound shown by the following general formula (5) (hereinafter may be referred to as "compound 5") to undergo a reaction in the presence of at least one of an alkali metal and an alkaline earth metal, for example. It is preferable to produce the compound 3 in a solvent. It is preferable to use an ether solvent in the same manner as in the case of producing the compound 1. For example, at least one of the alkali metal and the alkaline earth metal may be added to the solvent, and the compound 5 may be added to the mixture and reacted.

$$Si(OR^1)_{3-m}Y^1{}_m—R^2—X \quad (5)$$

wherein $R^1$, $R^2$, $Y^1$, X, and m are the same as defined for the general formula (3).

In this case, it is preferable to use the alkaline earth metal. It is preferable that the alkaline earth metal be magnesium. The compound 5 and magnesium are preferably mixed so that the amount of magnesium is 0.7 to 2.0 mol based on 1 mol of the compound 5. If the amount of magnesium is less than 0.7 mol, the raw material may be consumed to only a small extent. If the amount of magnesium is more than 2.0 mol, a large amount of magnesium may remain unreacted. The reaction temperature is preferably −15 to 100° C. If the reaction temperature is less than −15° C., the reaction rate may decrease. If the reaction temperature is more than 100° C., the reaction may not be controlled sufficiently.

1.3.2. Raw Material (Compound 4)

In the method of producing the organosilicon compound according to this embodiment, examples of the compound 4 that is the raw material for the compound 1 include methyltrimethoxysilane, methyltriethoxysilane, methyltriisopropoxysilane, methyltri-n-propoxysilane, methyltri isobutoxysilane, methyltri-n-butoxysilane, methyltriacetoxysilane, methyltriphenoxysilane, trimethoxysilane, triethoxysilane, trisopropoxysilane, tri-n-propoxysilane, triisobutoxysilane, tri-n-butoxysilane, triacetoxysilane, triphenoxysilane, ethyltrimethoxysilane, ethyltriethoxysilane, vinyltrimetoxysilane, vinyltriethoxysilane, phenyltrimethoxysilane, phenyltriethoxysilane, phenyltriisopropoxysilane, phenyltriacetoxysilane, dimethyldimethoxysilane, dimethyldiethoxysilane, dimethyldiisopropoxysilane, dimethyldi-n-propoxysilane, dimethyldiisobutoxysilane, dimethyldi-n-butoxysilane, dimethyldiacetoxysilane, dimethyldiphenoxysilane, methyldimethoxysilane, methyldiethoxysilane, methyldiisopropoxysilane, methyldi-n-propoxysilane, methyldiisobutoxysilane, methyldi-n-butoxysilane, methyldiacetoxysilane, methyldiphenoxysilane, methylphenyldimethoxysilane, methylphenyldiethoxysilane, methylphenyldiisopropoxysilane, diethyldimethoxysilane, diethyldiethoxysilane, methylvinyldimethoxysilane, methylvinyldiethoxysilane, and the like.

1.4. End Product (Compound 2)

In the method of producing the organosilicon compound according to this embodiment, the compound 2 that is the end product may be used to form an insulating film that includes silicon, carbon, oxygen, and hydrogen, for example. Such an insulating film exhibits high resistance to a hydrofluoric acid-based chemical widely used for a washing step during a semiconductor production process (i.e., exhibits high process resistance).

When using the compound 2 as an insulating film-forming material, it is preferable that the compound 2 have a content of each element (hereinafter may be referred to as "impurities")

other than silicon, carbon, oxygen, and hydrogen of 10 ppb or less, and a water content of 500 ppm or less, and more preferably 200 ppm or less. An insulating film that exhibits a low relative dielectric constant and excellent process resistance can be obtained in high yield by forming the insulating film using such a compound 2.

It is more preferable to use the compound 2 in which $R^4$ in the general formula (2) is a methyl group. Since the compound 2 in which $R^4$ in the general formula (2) is a methyl group has a low boiling point, the compound 2 can be conveniently used as a CVD material.

It is more preferable to use the compound 2 in which $R^2$ in the general formula (2) is a methylene group. When using the compound 2 in which $R^2$ in the general formula (2) is a methylene group, an insulating film that exhibits mechanical strength can be obtained.

1.5. Effects

The method of producing the organosilicon compound according to this embodiment can efficiently synthesize the compound 2 in high yield by a simple process. This effect is described in detail below.

When synthesizing the compound 2 without using the method of producing the organosilicon compound according to this embodiment, the compound 2 may be directly obtained by a Grignard reaction between a compound shown by the following general formula (8) (hereinafter may be referred to as "compound 8") and a compound shown by the following general formula (9) (hereinafter may be referred to as "compound 9"), for example.

wherein $R^4$ is the same as defined for the general formula (2), $Y^1$, $R^2$, and m are the same as defined for the general formula (1), and $M^1$ and n are the same as defined for the general formula (3).

wherein $R^4$ is the same as defined for the general formula (2), and $Y^2$ and X are the same as defined for the general formula (1).

However, when the compound 8 has a hydrolyzable group such as an alkoxy group, the compound 8 undergoes self-condensation during the Grignard reaction so that the compound 8 polymerizes. As a result, the yield of the compound 2 (i.e., reaction product) may decrease.

On the other hand, the product (compound 2) can be easily obtained in high yield by the method of producing the organosilicon compound according to this embodiment that substitutes the $OR^1$ group of the compound 1.

2. Examples and Comparative Examples

The invention is further described below by way of examples. Note that the invention is not limited to the following examples. In the examples and comparative examples, the unit "%" refers to "wt %" unless otherwise indicated.

2.1. Evaluation Method

The purity of the purified organosilane compound was determined using a gas chromatograph ("6890N" manufactured by Agilent Technologies, column: "SPB-35" manufactured by Supelco). The water content and the impurity content of the purified organosilane compound were measured using a Karl Fisher aquacounter ("AQ-7" manufactured by Hiranuma Sangyo Co., Ltd.) and an atomic absorption spectrophotometer (polarized Zeeman atomic absorption spectrophotometer "Z-5700" manufactured by Hitachi High-Technologies Corporation).

2.2. Synthesis Examples

2.2.1. Synthesis Example 1

A three-necked flask equipped with a cooling condenser and a dropping funnel was dried at 50° C. under reduced pressure, and was charged with nitrogen.

The flask was then charged with 400 g of chloromethyldichloromethylsilane, 400 g of pyridine, and 1200 g of diisopropyl ether. The mixture was stirred at 300 rpm for 15 minutes using a three-one motor. 350 g of isopropanol was then added to the mixture over two hours using a dropping funnel while cooling the mixture in an ice bath at 0° C. After the addition, the mixture was allowed to return to room temperature, and then stirred for two hours.

After the reaction, a hydrochloride obtained as a by-product was filtered using a Kiriyama funnel, and washed with 200 ml of hexane. The filtrate was concentrated under reduced pressure using an evaporator to obtain 415 g (yield: 80%) of chloromethylmethyldiisopropoxysilane (compound 5). The compound was purified by distillation.

2.2.2. Synthesis Example 2

2.2.2-1. Synthesis Example 2-1

A three-necked flask equipped with a cooling condenser and a dropping funnel was dried at 50° C. under reduced pressure, and was charged with nitrogen.

The flask was charged with 27.7 g of magnesium, followed by stirring for 10 minutes. After the addition of 96 g of tetrahydrofuran, 4.0 g of chloromethylmethyldiisopropoxysilane (compound 5) obtained in Synthesis Example 1 was added to the mixture at room temperature with stirring. A reaction started when 10 minutes had elapsed, and the temperature of the reaction solution increased to 50° C. After the addition of 150 g of tetrahydrofuran to the reaction solution, the reaction solution was immersed in a bath kept at 25° C., and stirred for five minutes.

A solution prepared by dissolving 196 g of chloromethylmethyldiisopropoxysilane (compound 5) obtained in Synthesis Example 1 in 200 g of tetrahydrofuran was then added dropwise to the reaction solution in the flask over 120 minutes. After the addition, the mixture was allowed to react at 25° C. for one hour to obtain a reaction solution containing methyl(diisopropoxy)silylmethylmagnesium chloride (compound 3).

150 g of methyltrimethoxysilane (compound 4) was added dropwise to the reaction solution over one hour. A gray precipitate was observed when about 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator, and then distilled to obtain 213 g (yield: 80%) of 4,4-dimethoxy-2,2-diisopropoxy-2,4-disilapentane (compound 1) as the end product.

The residual water content of the end product was 101 ppm. The content (metal impurity content) of elements other than silicon, carbon, oxygen, and hydrogen was as follows. Specifically, the Na content was 1.0 ppb, the K content was 1.5 ppb, and the Fe content was 1.3 ppb. The content of each of Li, Mg, Cr, Ag, Cu, Zn, Mn, Co, Ni, Ti, Zr, Al, Pb, Sn, and W was equal to or less than the detection limit (0.2 ppb).

2.2.2-2. Synthesis Example 2-2

A three-necked flask equipped with a cooling condenser and a dropping funnel was dried at 50° C. under reduced pressure, and was charged with nitrogen.

The flask was charged with 200 g of 4,4-dimethoxy-2,2-diisopropoxy-2,4-disilapentane (compound 1) obtained in Synthesis Example 2-1 and 200 g of methanol (compound 6), and the mixture was stirred for five minutes.

After the addition of 0.5 g of p-toluenesulfonic acid monohydrate, the mixture was allowed to react at room temperature for one hour. After the reaction, the resulting solution was placed in a recovery flask (2 l). The solution was then concentrated under reduced pressure using an evaporator to remove the solvent.

After the addition of 200 g of methanol, the mixture was allowed to react. The resulting solution was then concentrated. This step was then repeated twice. The product was then distilled to obtain 134 g (yield: 84%) of bis(dimethoxymethylsilyl)methane (compound 2) as the end product.

The residual water content of the end product was 120 ppm. The content (metal impurity content) of elements other than silicon, carbon, oxygen, and hydrogen was as follows. Specifically, the Na content was 1.0 ppb, the K content was 1.5 ppb, the Fe content was 1.3 ppb, and the Mg content was 1.0 ppb. The content of each of Li, Cr, Ag, Cu, Zn, Mn, Co, Ni, Ti, Zr, Al, Pb, Sn, and W was equal to or less than the detection limit (0.2 ppb).

2.2.3. Synthesis Example 3

2.2.3-1. Synthesis Example 3-1

A three-necked flask equipped with a cooling condenser and a dropping funnel was dried at 50° C. under reduced pressure, and was charged with nitrogen.

The flask was charged with 27.7 g of magnesium, followed by stirring for 10 minutes. After the addition of 96 g of tetrahydrofuran, 4.0 g of chloromethylmethyldiisopropoxysilane (compound 5) obtained in Synthesis Example 1 was added to the mixture at room temperature with stirring. A reaction started when 10 minutes had elapsed, and the temperature inside the flask increased to 50° C. After the addition of 150 g of tetrahydrofuran to the reaction solution, the reaction solution was immersed in a bath kept at 25° C., and stirred for five minutes.

A solution prepared by dissolving 196 g of chloromethylmethyldiisopropoxysilane (compound 5) in 200 g of tetrahydrofuran was then added dropwise to the reaction solution in the flask over 120 minutes. After the addition, the mixture was allowed to react at 25° C. for one hour to obtain a reaction solution containing methyl(diisopropoxy)silylmethylmagnesium chloride (compound 3).

140 g of dimethyldimethoxysilane (compound 4) was added dropwise to the reaction solution over one hour. A gray precipitate was observed when about 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator, and then distilled to obtain 196 g (yield: 78%) of 4-methyl-4-methoxy-2,2-diisopropoxy-2,4-disilapentane (compound 1) as the end product.

The residual water content of the end product was 155 ppm. The content (metal impurity content) of elements other than silicon, carbon, oxygen, and hydrogen was as follows. Specifically, the Na content was 1.1 ppb, the Fe content was 1.3 ppb, and the Mg content was 1.2 ppb. The content of each of K, Li, Cr, Ag, Cu, Zn, Mn, Co, Ni, Ti, Zr, Al, Pb, Sn, and W was equal to or less than the detection limit (0.2 ppb).

2.2.3-2. Synthesis Example 3-2

A three-necked flask equipped with a cooling condenser and a dropping funnel was dried at 50° C. under reduced pressure, and was charged with nitrogen.

The flask was charged with 150 g of 4-methyl-4-methoxy-2,2-diisopropoxy-2,4-disilapentane (compound 1) obtained in Synthesis Example 3-1 and 200 g of methanol (compound 6), and the mixture was stirred for five minutes.

After the addition of 0.4 g of p-toluenesulfonic acid monohydrate, the mixture was allowed to react at room temperature for one hour. After the reaction, the resulting solution was placed in a recovery flask (2 l). The solution was then concentrated under reduced pressure using an evaporator to remove the solvent.

After the addition of 150 g of methanol, the mixture was allowed to react. The resulting solution was then concentrated. This step was then repeated twice. The product was then distilled to obtain 95 g (yield: 81%) of 2,2,4-trimethoxy-4-methyl-2,4-disilapentane (compound 2) as the end product.

The residual water content of the end product was 111 ppm. The content (metal impurity content) of elements other than silicon, carbon, oxygen, and hydrogen was as follows. Specifically, the Mg content was 1.2 ppb, and the content of each of Na, K, Li, Fe, Cr, Ag, Cu, Zn, Mn, Co, Ni, Ti, Zr, Al, Pb, Sn, and W was equal to or less than the detection limit (0.2 ppb).

2.2.4. Synthesis Example 4

A three-necked flask equipped with a cooling condenser and a dropping funnel was dried at 50° C. under reduced pressure, and was charged with nitrogen.

The flask was then charged with 300g of (chloromethyl)chlorodimethylsilane, 400 g of pyridine, and 1000 g of t-butyl methyl ether. The mixture was stirred at 300 rpm for 15 minutes using a three-one motor. 300 g of t-butanol was added to the mixture over two hours using a dropping funnel while cooling the mixture in an ice bath at 0° C. After the addition, the mixture was allowed to return to room temperature, and then stirred for two hours.

After the reaction, a hydrochloride obtained as a by-product was filtered using a Kiriyama funnel, and washed with 200 ml of hexane. The filtrate was concentrated under reduced pressure using an evaporator to obtain 284 g (yield: 75%) of chloromethyldimethyl(t-butoxy)silane (compound 5).

2.2.5. Synthesis Example 5

2.2.5-1. Synthesis Example 5-1

A three-necked flask equipped with a cooling condenser and a dropping funnel was dried at 50° C. under reduced pressure, and was charged with nitrogen.

The flask was charged with 32.3 g of magnesium, followed by stirring for 10 minutes. After the addition of 96 g of tetrahydrofuran, 4.0 g of chloromethyldimethyl(t-butoxy)silane (compound 5) obtained in Synthesis Example 4 was added to the mixture at room temperature with stirring. A reaction started when 10 minutes had elapsed, and the temperature of the reaction solution increased to 50° C. After the addition of 150 g of tetrahydrofuran to the reaction solution, the reaction solution was immersed in a bath kept at 25° C., and stirred for five minutes.

A solution prepared by dissolving 186 g of chloromethyldimethyl(t-butoxy)silane (compound 5) in 200 g of tetrahydrofuran was then added dropwise to the reaction solution in the flask over 120 minutes. After the addition, the mixture was allowed to react at 25° C. for one hour to obtain a reaction solution containing dimethyl(t-butoxy)silylmethylmagnesium chloride (compound 3).

Then, 200 g of vinyltrimetoxysilane (compound 4) was added dropwise to the reaction solution over one hour. A gray precipitate was observed when about 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator, and then distilled to obtain 218 g (yield: 79%) of 5-(t-butoxy)-3,3-dimethoxy-5-methyl-3,5-disila-1-hexene (compound 1) as the end product.

The residual water content of the end product was 111 ppm. The content (metal impurity content) of elements other than silicon, carbon, oxygen, and hydrogen was as follows. Specifically, the Na content was 0.8 ppb, the K content was 0.9 ppb, and the Mg content was 1.2 ppb. The content of each of Li, Fe, Cr, Ag, Cu, Zn, Mn, Co, Ni, Ti, Zr, Al, Pb, Sn, and W was equal to or less than the detection limit (0.2 ppb).

2.2.5-2. Synthesis Example 5-2

A three-necked flask equipped with a cooling condenser and a dropping funnel was dried at 50° C. under reduced pressure, and was charged with nitrogen.

The flask was charged with 150 g of 5-(t-butoxy)-3,3-dimethoxy-5-methyl-3,5-disila-1-hexene (compound 1) obtained in Synthesis Example 5-1 and 150 g of methanol (compound 6), and the mixture was stirred for five minutes.

After the addition of 0.2 g of trifluoroacetic acid, the mixture was allowed to react at room temperature for one hour. After the reaction, the resulting solution was placed in a recovery flask (2 l). The solution was then concentrated under reduced pressure using an evaporator to remove the solvent.

After the addition of 150 g of methanol, the mixture was allowed to react. The resulting solution was then concentrated. This step was then repeated twice. The product was then distilled to obtain 121 g (yield: 82%) of 3,3,5-trimethoxy-5-methyl-3,5-disila-1-hexene (compound 2) as the end product.

The residual water content of the end product was 111 ppm. The content (metal impurity content) of elements other than silicon, carbon, oxygen, and hydrogen was as follows. Specifically, the Na content was 0.8 ppb, the K content was 0.9 ppb, the Fe content was 0.5 ppb, and the Ni content was 1.0 ppb. The content of each of Li, Fe, Cr, Ag, Cu, Zn, Mn, Co, Ti, Zr, Al, Pb, Sn, and W was equal to or less than the detection limit (0.2 ppb).

2.2.6. Synthesis Example 6

2.2.6-1. Synthesis Example 6-1

A three-necked flask equipped with a cooling condenser and a dropping funnel was dried at 50° C. under reduced pressure, and was charged with nitrogen.

The flask was charged with 32.3 g of magnesium, followed by stirring for 10 minutes. After the addition of 96 g of tetrahydrofuran, 4.0 g of chloromethyldimethyl(t-butoxy)silane (compound 5) obtained in Synthesis Example 4 was added to the mixture at room temperature with stirring. A reaction started when 10 minutes had elapsed, and the temperature of the reaction solution increased to 50° C. After the addition of 150 g of tetrahydrofuran to the reaction solution, the reaction solution was immersed in a bath kept at 25° C., and stirred for five minutes.

A solution prepared by dissolving 186 g of chloromethyldimethyl(t-butoxy)silane (compound 5) in 200 g of tetrahydrofuran was then added dropwise to the reaction solution in the flask over 120 minutes. After the addition, the mixture was allowed to react at 25° C. for one hour to obtain a reaction solution containing dimethyl(t-butoxy)silylmethylmagnesium chloride (compound 3).

Then, 250 g of ethyltrimethoxysilane (compound 4) was added dropwise to the reaction solution over one hour. A gray precipitate was observed when about 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator to obtain 218 g (yield: 79%) of 2-(t-butoxy)-4,4-dimethoxy-2-methyl-2,4-disilahexane (compound 1) as the end product.

2.2.6-2. Synthesis Example 6-2

A three-necked flask equipped with a cooling condenser and a dropping funnel was dried at 50° C. under reduced pressure, and was charged with nitrogen.

The flask was charged with 150 g of 2-(t-butoxy)-4,4-dimethoxy-2-methyl-2,4-disilahexane (compound 1) obtained in Synthesis Example 6-1 and 150 g of methanol (compound 6), and the mixture was stirred for five minutes.

After the addition of 0.4 g of p-toluenesulfonic acid monohydrate, the mixture was allowed to react at room temperature for one hour. After the reaction, the resulting solution was placed in a recovery flask (2 l). The solution was then concentrated under reduced pressure using an evaporator to remove the solvent.

After the addition of 150 g of methanol, the mixture was allowed to react. The resulting solution was then concentrated. This step was then repeated twice. The product was then distilled to obtain 102 g (yield: 81%) of 2,4,4-trimethoxy-2-methyl-2,4-disilahexane (compound 2) as the end product.

The residual water content of the end product was 111 ppm. The content (metal impurity content) of elements other than silicon, carbon, oxygen, and hydrogen was as follows. Specifically, the Na content was 0.9 ppb, the Fe content was 1.5 ppb, the Ni content was 1.0 ppb. The content of each of K, Li, Fe, Cr, Ag, Cu, Zn, Mn, Co, Ti, Zr, Al, Pb, Sn, and W was equal to or less than the detection limit (0.2 ppb).

2.2.6-3. Synthesis Example 6-3

A three-necked flask equipped with a cooling condenser and a dropping funnel was dried at 50° C. under reduced pressure, and was charged with nitrogen.

The flask was charged with 150 g of 2-(t-butoxy)-4,4-dimethoxy-2-methyl-2,4-disilahexane (compound 1)

obtained in Synthesis Example 6-1 and 250 g of methanol (compound 6), and the mixture was stirred for five minutes.

After the addition of 0.4 g of p-toluenesulfonic acid monohydrate, the mixture was allowed to react at room temperature for one hour. After the reaction, the resulting solution was placed in a recovery flask (2 l). The solution was then concentrated under reduced pressure using an evaporator to remove the solvent.

After the addition of 250 g of methanol, the mixture was allowed to react. The resulting solution was then concentrated. This step was then repeated four times. The product was then distilled to obtain 127 g (yield: 85%) of 2,4,4-triethoxy-2-methyl-2,4-disilahexane (compound 2) as the end product.

The residual water content of the end product was 111 ppm. The content (metal impurity content) of elements other than silicon, carbon, oxygen, and hydrogen was as follows. Specifically, the Na content was 1.3 ppb, the K content was 1.2 ppb, the Fe content was 1.5 ppb, and the Ni content was 1.0 ppb. The content of each of Li, Fe, Cr, Ag, Cu, Zn, Mn, Co, Ti, Zr, Al, Pb, Sn, and W was equal to or less than the detection limit (0.2 ppb).

2.2.7. Comparative Synthesis Example 1

A three-necked flask equipped with a cooling condenser and a dropping funnel was dried at 50° C. under reduced pressure, and was charged with nitrogen.

The flask was charged with 29.04 g of magnesium, followed by stirring for 10 minutes. After the addition of 96 g of tetrahydrofuran, 4.0 g of chloromethylmethyldimethoxysilane (raw material for the compound 8) was added to the mixture at room temperature with stirring. A reaction started when 10 minutes had elapsed, and the temperature of the reaction solution increased to 50° C. After the addition of 150 g of tetrahydrofuran to the reaction solution, the reaction solution was immersed in a bath kept at 25° C., and stirred for five minutes.

A solution prepared by dissolving 176 g of chloromethylmethyldimethoxysilane (raw material for the compound 8) and 250 g of methyltrimethoxysilane (compound 9) in 200 g of tetrahydrofuran was then added dropwise to the reaction solution in the flask over 120 minutes. A gray precipitate was observed when 20 minutes had elapsed after the start of addition. After the addition, the temperature of the bath was increased to 70° C., and the mixture was allowed to react for three hours.

After the reaction, a magnesium salt obtained as a by-product was filtered using a Kiriyama funnel, and washed with 200 ml of hexane. The filtrate was concentrated under reduced pressure using an evaporator, and then distilled to obtain 10 g (yield: 3.8%) of bis(dimethoxymethylsilyl)methane (compound 2) as the end product.

Table 1 shows the total yield (%) and the purity (%) of the end product (compound 2). In Table 1, Examples 1, 2, 3, 4, and 5 respectively correspond to Synthesis Examples 2, 3, 5, 6-1, and 6-2, and Comparative Example corresponds to Comparative Synthesis Example 1.

Note that the term "end product total yield (%)" shown in Table 1 refers to the product of the yield when synthesizing the compound 1 from the compound 5 and the yield when synthesizing the compound 2 from the compound 1.

TABLE 1

|  | End product total yield (%) | Purity |
|---|---|---|
| Example 1 | 67 | 99.9 |
| Example 2 | 63 | 99.8 |
| Example 3 | 65 | 99.9 |
| Example 4 | 64 | 99.9 |
| Example 5 | 67 | 99.7 |
| Comparative Example | 4 | 99.5 |

As shown in Table 1, when carrying out a Grignard reaction using the halogen silane monomer (compound 5) having a bulky alkoxy group (Examples 1 to 5), self-condensation of the halogen silane monomer could be suppressed to obtain an alkoxysilane monomer (compound 1). In the subsequent step of converting the bulky alkoxy group of the alkoxysilane monomer into a lower alkoxy group (conversion from the compound 1 to the compound 2), the target organosilane compound (compound 2) could be obtained as a single product in high yield.

On the other hand, when carrying out a Grignard reaction using the halogen silane monomer having a lower alkoxy group (Comparative Example), since the halogen silane monomer underwent self-condensation, the organosilane compound (compound 2) (end product) could not be obtained as a single product.

The embodiments according to the invention have been described above. The invention includes configurations substantially the same as the configurations described relating to the above embodiments (in function, in method and effect, or in objective and effect). The invention also includes a configuration in which an unsubstantial element of the above embodiments is replaced by another element. The invention also includes a configuration having the same effects as those of the configurations described relating to the above embodiments, or a configuration capable of achieving the same object as those of the above-described configurations. The invention further includes a configuration obtained by adding known technology to the configurations described in the above embodiments.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. A method of producing an organosilicon compound comprising substituting at least an $OR^1$ group of a compound shown by the following general formula (1) to obtain a compound shown by the following general formula (2),

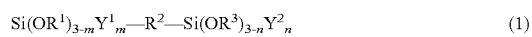

$$Si(OR^1)_{3-m}Y^1{}_m-R^2-Si(OR^3)_{3-n}Y^2{}_n \qquad (1)$$

wherein $R^1$ individually represents a substituted or unsubstituted alkyl group having 3 to 10 carbon atoms, a substituted or unsubstituted alkenyl group having 3 to 10 carbon atoms, a substituted or unsubstituted alkynyl group having 3 to 10 carbon atoms, or a substituted or unsubstituted aryl group having 6 to 12 carbon atoms, $Y^1$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, $R^2$ individually represents a substituted or unsubstituted methylene group, a substituted or unsubstituted alkylene group having 2 to 6 carbon atoms, a substituted or unsubstituted alkenylene group having 2 to 6 carbon atoms, a substituted or unsubstituted alkynylene group having 2 to 6 carbon atoms, or a substituted or unsubstituted arylene group having 6 to 12 carbon atoms, m represents an integer from 0 to 2, $R^3$ individually represents a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group having 6 to 12 carbon atoms, or a substituted or unsubstituted acyl group having 1 to 10 carbon atoms, $Y^2$ individually represents a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group having 6 to 12 carbon atoms, and n represents an integer from 0 to 2, $$Si(OR^4)_{3-m}Y^1{}_m\text{—}R^2\text{—}Si(OR^4)_{3-n}Y^2{}_n \tag{2}$$

wherein $R^4$ individually represents an alkyl group having 1 or 2 carbon atoms or an alkenyl group, and $R^2$, $Y^1$, $Y^2$, m, and n are the same as defined for the general formula (1).

2. The method of producing an organosilicon compound according to claim 1, further comprising reacting at least one compound shown by the following general formula (3) with a compound shown by the following general formula (4) to obtain the compound shown by the general formula (1), $$Si(OR^1)_{3-m}Y^1{}_m\text{—}R^2\text{-}M^1X \tag{3}$$

wherein $R^1$, $R^2$, $Y^1$, and m are the same as defined for the general formula (1), $M^1$ represents an alkali metal or an alkaline earth metal, and X represents a halogen atom, $$Si(OR^3)_{4-n}Y^2{}_n \tag{4}$$

wherein $R^3$, $Y^2$, and n are the same as defined for the general formula (1).

3. The method of producing an organosilicon compound according to claim 1, wherein the $OR^1$ group is substituted by reacting the compound shown by the general formula (1) with at least one of a compound shown by the following general formula (6) and a compound shown by the following general formula (7), $$R^4OH \tag{6}$$

wherein $R^4$ is the same as defined for the general formula (2), $$(R^4O)_rM^2 \tag{7}$$

wherein $M^2$ represents an alkali metal or an alkaline earth metal, r represents the valence of the alkali metal or the alkaline earth metal represented by $M^2$, and $R^4$ is the same as defined for the general formula (2).

4. The method of producing an organosilicon compound according to claim 1, wherein the $OR^1$ group is substituted in the presence of an acid catalyst or an alkali catalyst.

5. The method of producing an organosilicon compound according to claim 1, wherein $R^2$ in the general formula (1) and the general formula (2) is a methylene group.

6. The method of producing an organosilicon compound according to claim 1, wherein $R^4$ in the general formula (2) is a methyl group.

7. The method of producing an organosilicon compound according to claim 2, further comprising causing a compound shown by the following general formula (5) to undergo a reaction in the presence of at least one of an alkali metal and an alkaline earth metal to obtain the compound shown by the general formula (3), $$Si(OR^1)_{3-m}Y^1{}_m\text{—}R^2\text{—}X \tag{5}$$

wherein $R^1$, $R^2$, $Y^1$, and m are the same as defined for the general formula (1), and X is the same as defined for the general formula (3).

8. The method of producing an organosilicon compound according to claim 7, wherein the alkaline earth metal is magnesium.

* * * * *